US008425586B2

(12) United States Patent
Leopold et al.

(10) Patent No.: US 8,425,586 B2
(45) Date of Patent: Apr. 23, 2013

(54) VASCULAR PROSTHESIS WITH STRESS RELIEF SLOTS

(75) Inventors: Eric W. Leopold, Redwood City, CA (US); Gerald Ray Martin, Redwood City, CA (US); Eric Hsiang Yu, Morage, CA (US); Alexander Arthur Lubinski, Rocklin, CA (US); Michael C. Waldo, San Jose, CA (US); Christopher P. Cheng, Palo Alto, CA (US)

(73) Assignee: NovoStent Corporation, San Francisco, CA (US)

( * ) Notice: Subject to any disclaimer, the term of this patent is extended or adjusted under 35 U.S.C. 154(b) by 90 days.

(21) Appl. No.: 12/870,700

(22) Filed: Aug. 27, 2010

(65) Prior Publication Data

US 2011/0054590 A1 Mar. 3, 2011

Related U.S. Application Data

(60) Provisional application No. 61/239,351, filed on Sep. 2, 2009.

(51) Int. Cl.
*A61F 2/82* (2006.01)

(52) U.S. Cl.
USPC .......................................................... 623/1.15

(58) Field of Classification Search ................. 623/1.15, 623/1.35; *A61F 2/06, 2/82*
See application file for complete search history.

(56) References Cited

U.S. PATENT DOCUMENTS

| | | | |
|---|---|---|---|
| 5,041,126 A | 8/1991 | Gianturco | |
| 5,441,515 A | 8/1995 | Khosravi et al. | |
| 5,603,722 A | 2/1997 | Phan et al. | |
| 5,607,445 A | 3/1997 | Summers | |
| 5,632,771 A | 5/1997 | Boatman et al. | |
| 5,707,387 A | 1/1998 | Wijay | |
| 5,824,052 A | 10/1998 | Khosravi et al. | |
| 5,861,027 A | 1/1999 | Trapp | |
| 5,897,588 A | 4/1999 | Hull et al. | |
| 5,984,963 A | 11/1999 | Ryan et al. | |
| 6,015,433 A | 1/2000 | Roth | |
| 6,080,191 A | 6/2000 | Summers | |
| 6,273,908 B1 | 8/2001 | Ndondo-Lay | |

(Continued)

OTHER PUBLICATIONS

International Search Report and Written Opinion of the International Searching Authority; PCT/US2010/047449; Oct. 20, 2010; 13 pgs.

*Primary Examiner* — Thomas J Sweet
*Assistant Examiner* — Jason-Dennis Stewart
(74) *Attorney, Agent, or Firm* — James F. Hann; Haynes Beffel & Wolfeld LLP

(57) ABSTRACT

A vascular prosthesis comprises generally tubular body placeable in contracted and expanded states and has an axial length and a circumferential dimension in the expanded state. The body includes a series of circumferential elements having first lengths. First and second connectors have connector lengths and join alternating ends of adjacent circumferential elements. The first length plus the connector lengths joined thereto equal a total circumferential length. Each connector length is between 2.5% and 25% of the total circumferential length. Adjacent circumferential elements and connectors extending therefrom are separated by a stress relief slot having a relief slot length of more than 50% and less than 95% of the total circumferential length. The stress relief slots have narrow width portions over a majority of the relief slot lengths, the narrow width portions having lateral dimensions of no greater than about 3 mm.

31 Claims, 17 Drawing Sheets

U.S. PATENT DOCUMENTS

| | | |
|---|---|---|
| 6,273,910 B1 | 8/2001 | Limon |
| 6,409,752 B1 | 6/2002 | Boatman et al. |
| 2002/0004679 A1 | 1/2002 | Eury et al. |
| 2003/0088310 A1 | 5/2003 | Hansen et al. |
| 2003/0120335 A1 | 6/2003 | Ehr et al. |
| 2004/0102837 A1 | 5/2004 | Boyle et al. |
| 2005/0149164 A1* | 7/2005 | Rivelli ............ 623/1.11 |
| 2005/0163821 A1 | 7/2005 | Sung et al. |
| 2007/0185560 A1* | 8/2007 | Roeder et al. ............ 623/1.15 |
| 2007/0213805 A1 | 9/2007 | Schaeffer et al. |
| 2008/0183275 A1 | 7/2008 | Schmid et al. |
| 2008/0221658 A1 | 9/2008 | Martin et al. |
| 2008/0221663 A1 | 9/2008 | Leopold et al. |
| 2009/0105806 A1 | 4/2009 | Benjamin et al. |
| 2009/0326639 A1 | 12/2009 | Edin |
| 2010/0030319 A1* | 2/2010 | Weber ............ 623/1.11 |

* cited by examiner

VASCULAR PROSTHESIS WITH STRESS RELIEF SLOTS

CROSS-REFERENCE TO OTHER APPLICATIONS

This application claims the benefit of U.S. provisional patent application No. 61/239,351, filed on 2 Sep. 2009, entitled Serpentine Vascular Prosthesis, the disclosure of which is incorporated by reference.

This application is related to commonly assigned US patent application publication number US 2008/0221663 A1, published 11 Sep. 2008.

BACKGROUND OF INVENTION

Today, there are a wide range of intravascular prostheses on the market for use in the treatment of aneurysms, stenosis, and other vascular disease. Balloon-expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath or a release wire, then self-expand when the sheath or release wire is retracted. Slotted-tube stent designs typically have relatively thick struts in folding cell patterns in order to obtain a sufficient strength when deployed. In the absence of separate, costly marker bands, slotted tube stents also require thick struts for the stent to be radiopaque under x-ray imaging. Accordingly, such stents may not be suitable for use in smaller vessels, such as cerebral vessels and coronary arteries where device profile is more critical. The thick struts have also been know to cause disruptive local turbulence of blood flow in an artery, which results in negative cellular response including restenosis. An alternate stent made in a helical pattern may have a thin strut and a high surface area density for radiopacity, while also having desired strength, but may have larger than desired profile due to overlapping in the wound down state. It is desirable to have a thin strut stent design that minimizes overall delivery profile and optimizes delivery flexibility, strength, and radiopacity.

Stents also face challenges with limited vessel area coverage, resulting in poor scaffolding and subsequent restenosis. The limited vessel coverage also prohibits the use of current stents in the treatment of aneurysms. While covered stent grafts may be used, they are often restricted from use around vessels with side branches or bifurcations.

Further, slotted tube stents have suffered from poor in vivo performance in vasculature with challenging biomechanics such as the superficial femoral artery (SFA). When used in the treatment of the SFA, stents may have insufficient radial force, resulting in poor patency and restenosis. Additionally, repetitive lateral loading and unloading of a stent in the SFA have been known to cause fatigue-induced strut failure, which may contribute to restenosis and subsequent vessel narrowing and/or occlusion. Therefore, stents are desired to be configured to provide a high radial strength while also providing adequate flexibility. However, providing additional radial strength has generally resulted in a reduction in the flexibility of the stent.

Various techniques may be utilized to characterize those attributes of stents such as measuring a displacement response for a given force or determining elastic modulus. For example, radial strength may be characterized by determining the amount of force required to radially compress a stent a given distance and determining the stiffness (referred to herein as "Krad"). Alternatively, radial strength may be characterized by determining an amount of force applied linearly by opposing plates to compress a stent a given distance and determining the stiffness (referred to herein as "Kfp"). The flexibility of a stent may be characterized by measuring the amount of force required to cause a given length of axial extension and determining the stiffness (referred to herein as "Kax"). Alternatively, the flexibility may be characterized by measuring the lateral deflection of a stent in response to a lateral force applied to a free end of the stent to determine stiffness (referred to herein as "Klat").

A ratio of the stiffness characterizations of radial strength to flexibility may be used to provide a comparison of stents having different structures. For example, it has been found that a selected sample of currently commercially available stents generally possess Krad/Kax ratios in the range of 5-10, Krad/Klat ratios in the range of 148-184, Kfp/Kax ratios in the range of 1-6 and Kfp/Klat ratios in the range of 40-113 based on test samples each having approximately a 0.236 inch diameter, 0.906 inch length and a 0.008 inch wall thickness. It would be desirable to have a structure that provides greater ratios so that a more optimum combination of radial strength and flexibility is provided.

U.S. Pat. No. 5,707,387 to Wijay describes a stent constructed from a plurality of bands, where each band is composed of a solid wire-like material formed into a closed, substantially rectangular shape. Each band is circumferentially offset from the adjacent band and adjacent bands are connected by one or more cross-tie members. This stent has several drawbacks. The rectangular cell design does not allow for longitudinal loading because the cells are not flexible. Therefore, under a longitudinal load, the apex will move out of plane and be biased into the vessel (i.e. into the vessel flow). Secondly, the stent may be susceptible to fracture with repetitive loading and unloading because of the rigid cells.

When utilizing stents in interventional procedures, it may be advantageous to deliver therapeutic agents to a vessel wall via coating on the surface of the stent. Drug eluting stents have many advantages in reducing the rates of restenosis. Typically, the drug is disposed in the matrix of a polymer coating on the struts of the stents, and then gradually released into the surrounding tissue. The uniform delivery of the drug is typically limited by the overall surface area or coverage of the stent and the proximity between struts.

In traditional slotted-tube stent designs, when deployed at the treatment diameter, large gapping between struts and low surface coverage occur as a result of the expansion from the collapsed state, typically resulting in 25% and lower metal coverage. Drug delivery from the stent struts is therefore limited by the low surface coverage of the stent.

Spiraling mesh ribbon stent designs provide certain benefits over slotted-tube stent designs for scaffolding, surface area coverage, and radial stiffness. However, such stent designs also face limitations. First, some spiralling mesh ribbon stent designs, when retained in the delivery system, face challenges with device profile as a result of multiple wound layers. While having a helical style stent not overlapped in the wound-down state reduces profile, it results in a substantial length change with the stent substantially foreshortening upon deployment. Therefore, it is advantageous to design a lower profile stent by reducing the number of layers resulting in the wrapped-for-delivery stent.

In addition, during stent deployment using an outer sheath retraction mechanism, spiraling mesh ribbon designs are susceptible to axially collapsing of the wrapped stent. A design with thin stent wall thickness may result in axially adjacent layers slipping over each other. In the constrained state, it is critical for the stent to have the axial compressive stiffness to withstand the load applied by the outer sheath during deployments. It is also important that layers remain well-aligned during stent deployment. Proper layer-layer alignment helps to resist layers shifting out of plane and the resulting disruption to deployment mechanics or high deployment forces.

Another challenge to spiraling mesh ribbon designs is achieving a successful stent deployment with the stent fully apposed to the vessel wall. One mechanism of deployment is for current helical stent platforms to unwind from the constrained state inside a catheter, either by rotating the delivery system or by allowing the stent to freely open. The unwinding sequence may be disrupted by vessel narrowings or the catching of layers, resulting in stent narrowings, which may be prohibitive to post-stent balloon dilatation. In order to successfully balloon a helical winding, it is necessary to unwind the helical section and transpose the material either distally or proximally along the stent. This can lead to a disruption in the stent apposition in these areas or be unsuccessful in creating permanent apposition. It is desirable to create a stent with less unwinding required and a counter-wind to absorb the effect of ballooning.

Deployment of spiraling mesh ribbon designs may also be challenging with respect to deployment force. Using the conventional sheath-withdrawal mechanism for self-expanding stent deployment, the outward acting forces of the multiple layers of the constrained stents may result in embedding effects inside the outer sheath, particularly after sterilization or storage-time related creep. Therefore, it would be beneficial to incorporate stent design features to lower the outward acting force of the stent when constrained in the catheter sheath and design elements to minimize stent embedding into the sheath.

Processing of mesh ribbon designs inside a catheter poses another challenge. Mesh ribbon designs typically need to be wound in order to diametrically reduce the profile of the device, thus making conventional crimping processes challenging to incorporate. Thus, it is desirable to integrate features in the design that facilitate the ability to process the prosthesis inside a small-profile catheter.

The flexibility of some spiraling mesh-ribbon stent designs is deficient as well. In one example, U.S. Pat. No. 5,603,722 to Phan et al. describes a stent formed of expandable strip-like segments. The strip-like segments are joined along side regions in a ladder-like fashion along offsetting side regions. A shortcoming of such a stent is that the junctions between adjacent segments are not provided with a means of addressing longitudinal loading. In another example, U.S. Pat. No. 5,632,771 to Boatman et al., the helical stent design has a solid backbone down the length, prohibiting the stent from elongating or foreshortening. In both cases, the result of high axial stiffness is that the stent is susceptible to strut fracture.

In view of the drawbacks of previously known devices, it would be desirable to provide an implantable vascular prosthesis with thin struts, optimal delivery flexibility and profile, robust opening dynamics amenable to post-stent balloon dilatation, high radial stiffness to flexibility ratio, longitudinal flexibility, good radiopacity, and a high surface area for both drug delivery and scaffolding, while allowing blood flow to side branch vessels.

BRIEF SUMMARY OF THE INVENTION

A vascular prosthesis comprises generally tubular body defining an axis. The body is placeable in contracted and expanded states and has an axial length and a circumferential dimension in the expanded state. The body includes a series of circumferential elements and first and second connectors. The circumferential elements include at least first, second, third and fourth circumferential elements. Each circumferential element has first and second ends. The first and second ends are circumferentially spaced apart. Each circumferential element has a circumferentially-extending first length between the first and second ends. The first and second connectors join alternating ends of adjacent circumferential elements so that first connectors join the first ends of the first and second circumferential elements and the first ends of the third and fourth circumferential elements. A second connector joins the second ends of the second and third circumferential elements, thereby creating a generally serpentine pattern of the circumferential elements and connectors. The first and second connectors have circumferentially-extending first and second connector lengths. The first length plus the first and second connector lengths joined thereto equal a total circumferential length. Each connector length is between 2.5% and 25% of the total circumferential length so that axial flexibility is provided for the body without sacrificing deployment dynamics. The second and third circumferential elements and the first connectors at the first ends of the second and third circumferential elements are separated by a stress relief slot. Each stress relief slot has a circumferentially-extending relief slot length of more than 50% and less than 95% of the total circumferential length. The stress relief slots have narrow width portions over a majority of the relief slot lengths, the narrow width portions having lateral dimensions of no greater than about 3 mm. In some examples, the circumferential elements and the connectors are essentially rectangular. In some examples, the narrow width portion has a lateral dimension of less than 1 mm. In some examples, the narrow width portions extend over essentially the entire relief slot lengths.

Other features, aspects and advantages of the present invention can be seen on review the figures, the detailed description, and the claims which follow.

DETAILED DESCRIPTION OF THE INVENTION

Figure 1:
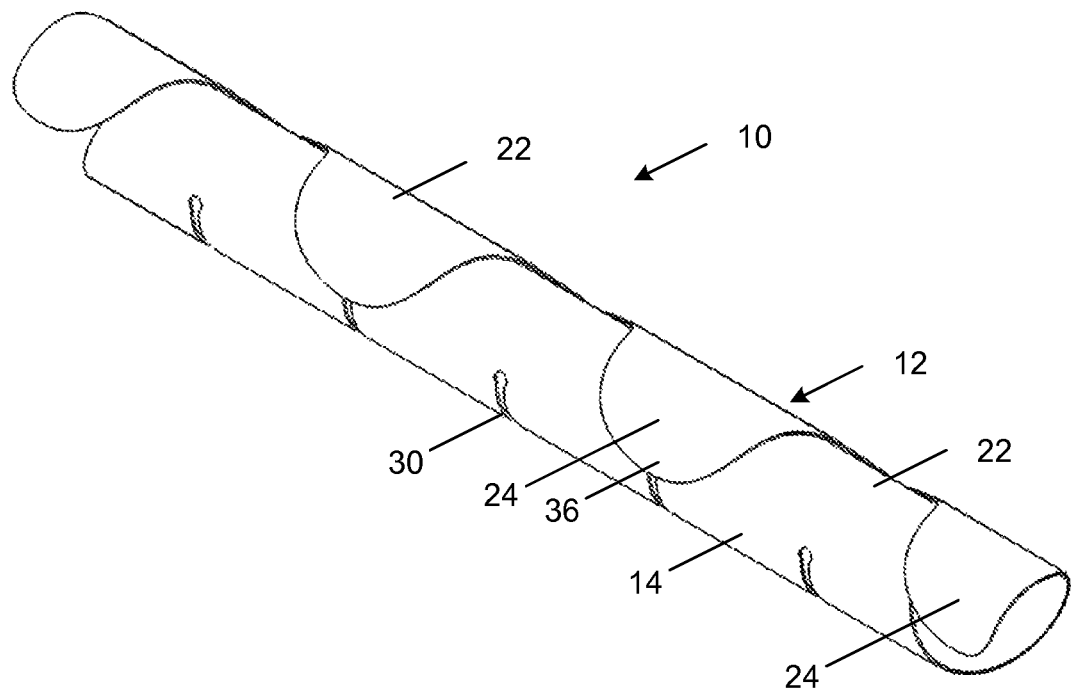
FIG. 1 is an overall view of a vascular prosthesis made according to the invention in a deployed, expanded state with overlapped edges.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

Figure 2:
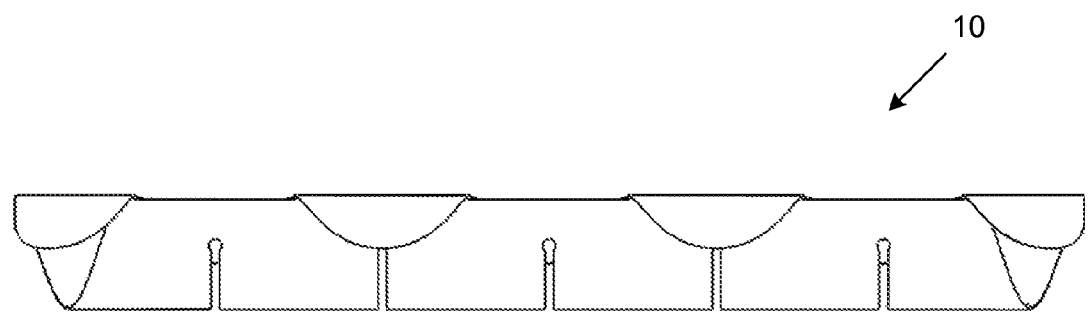
FIG. 2 is a side view of the prosthesis of FIG. 1.
Figure 3:
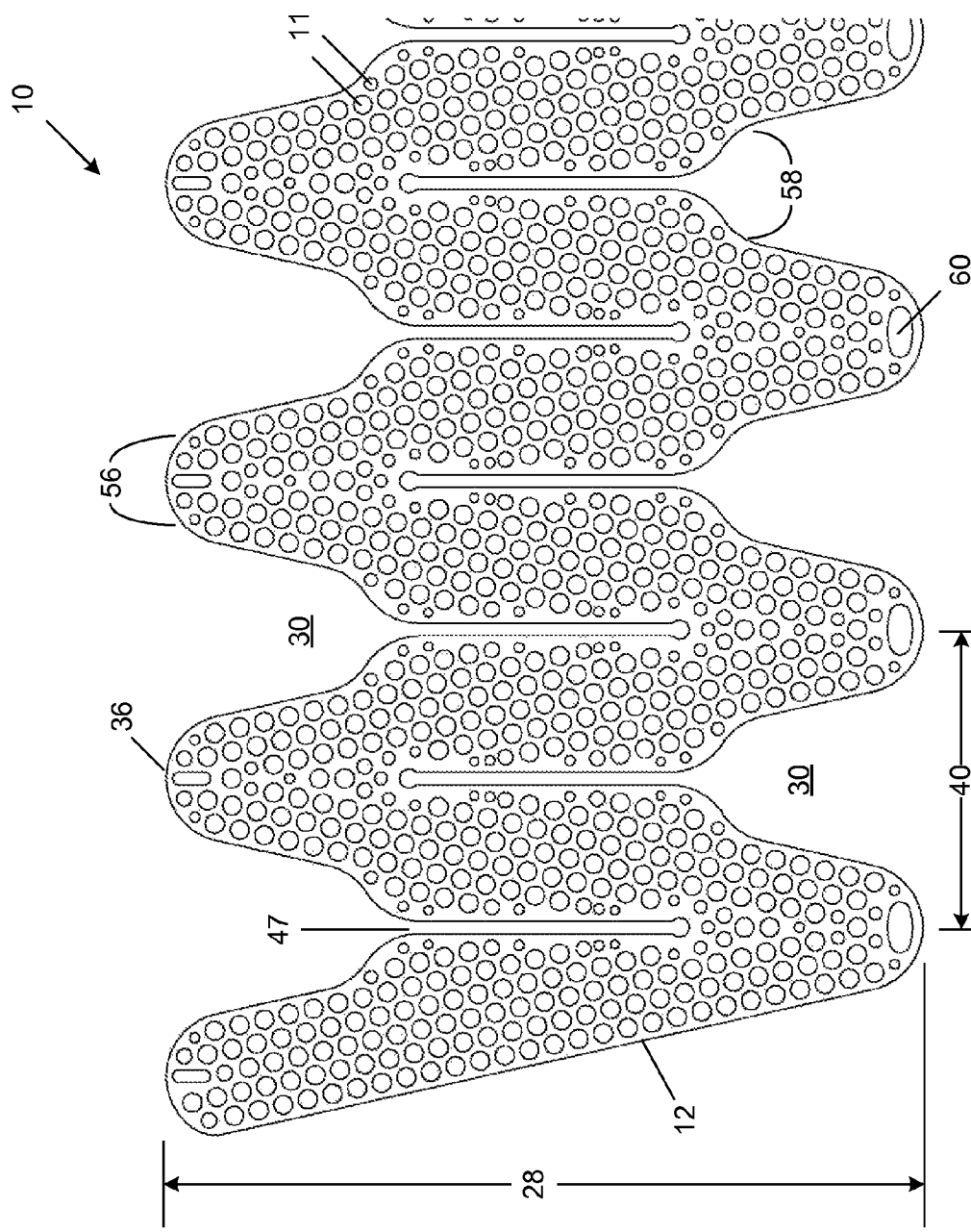
FIG. 3 is an enlarged view of a portion of the prosthesis of FIG. 1 and a flattened, rolled out state illustrating the pattern of openings, which are not shown in FIGS. 1 and 2.
Figure 4:
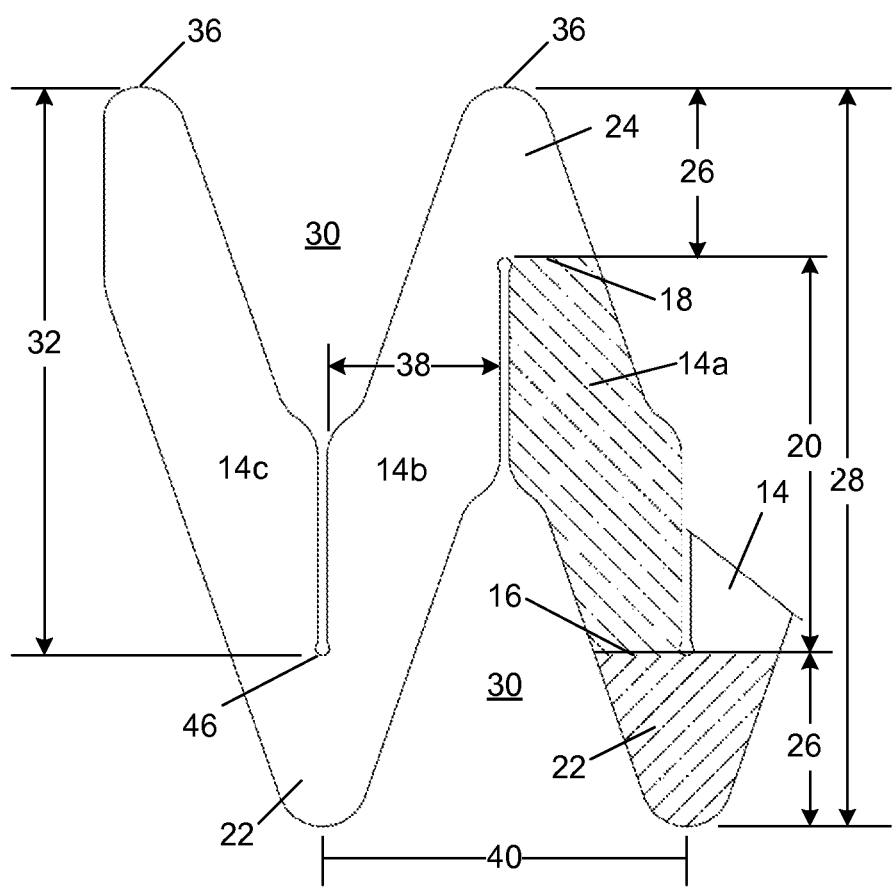
FIGS. 4 and 5 illustrate other examples of the prosthesis of FIG. 1 and are used to define various portions of the prosthesis.
Figure 5:
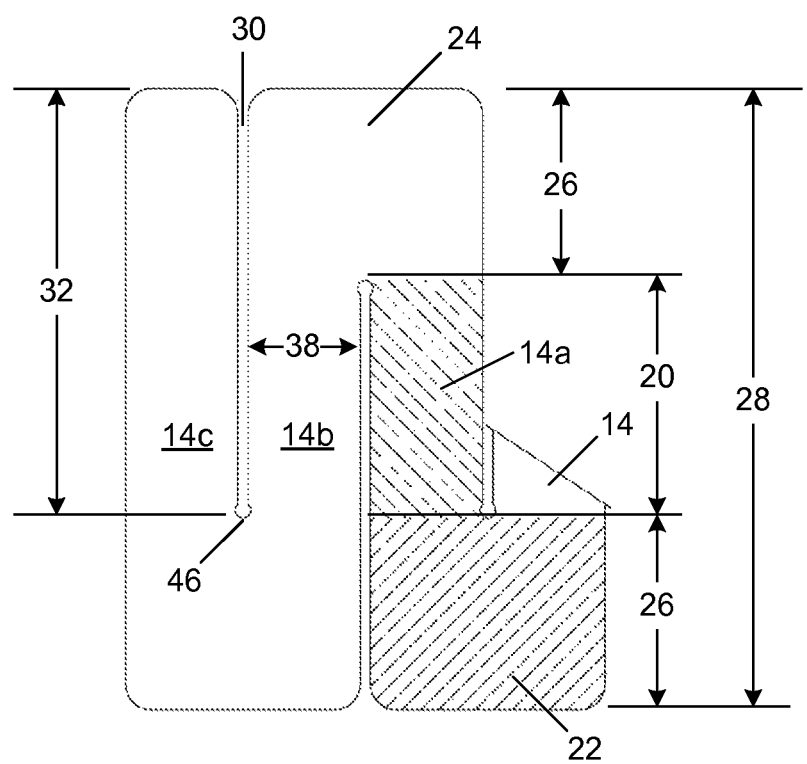

FIGS. 1 and 2 show one example of a vascular prosthesis 10 in a deployed configuration with overlapped edges. FIG. 3 is an enlarged view of a portion of the vascular prosthesis of FIGS. 1 and 2 in a rolled out or flattened state. In FIGS. 1 and 2 and other figures in this application, vascular prosthesis 10 is commonly illustrated as a solid structure for ease of illustration. However, in many if not most cases it will be a structure such as illustrated in FIG. 3 having openings 11, typically through holes, formed therein. FIGS. 4 and 5, illustrating other examples, are used to define various portions of vascular prosthesis 10. Vascular prosthesis 10 comprises a generally tubular body 12. Tubular body 12 includes a number of circumferential elements 14, each circumferential element having a first end 16 and a second end 18. First and second ends 16, 18 are circumferentially spaced apart with the circumferential element 14 having a circumferentially-extending first length 20, sometimes referred to as height 20, between the first and second ends.

First and second connectors 22, 24 join alternating first and second ends 16, 18 ends of adjacent circumferential elements 14. Therefore, first connectors 22 join the first ends 16 of the adjacent circumferential elements 14, 14a and the first ends of adjacent circumferential elements 14b, 14c. Also, second connector 24 joins the second ends 18 of the second and third circumferential elements 14a, 14b. This relationship continues along vascular prosthesis 10 thereby creating a generally serpentine pattern of the circumferential elements 14 and connectors 22, 24 of vascular prosthesis 10. Thus, vascular prosthesis 10 comprises a plurality of circumferential stent elements that are joined by connecting elements in an alternating pattern, wherein the prosthesis is to be implanted into a body lumen with applications including, but not limited to, supporting the patency of the body lumen and/or drug delivery to the site of implant.

First and second connectors 22, 24 have circumferentially extending connector lengths 26 which are typically of equal length but could be of different lengths. The total of length 20 and connector lengths 26 for the first and second connectors 22, 24 constitute the total circumferential length 28. The adjacent circumferential elements, such as second and third circumferential elements 14a, 14b, and the first connectors 22 at the first ends 16 of the second and third circumferential elements, are separated by a stress relief slot 30. Each stress relief slot 30 has a circumferentially-extending relief slot length 32. Length 32 is preferably more than 50% and less than 95% of the total circumferential length 28. The stress relief slots 30 have narrow width portions 34 over a substantial portion, preferably a majority, of the relief slot lengths 32. Having length 32 more than 50% of total circumferential length 28 is important to eliminate the creation of a backbone, found with some conventional stents, which effectively eliminates axial flexibility. Having length 32 be less than 95% of total circumferential length 28 is important to ensure adequate strength for vascular prosthesis 10.

Figure 1A:
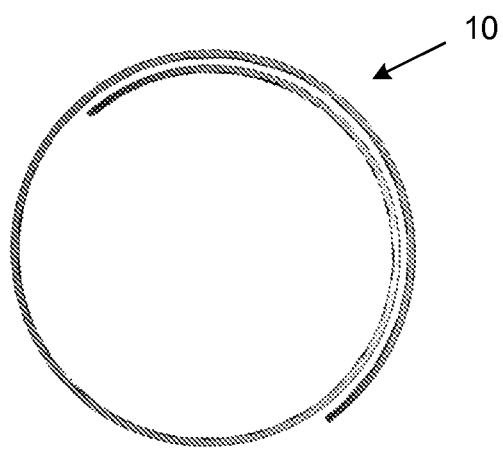
FIG. 1A is a simplified cross-sectional view of the prosthesis FIG. 1.

FIGS. 1, 1A, and 2 depict prosthesis 10 in a deployed state with the convex edges 56 at the tip 36 of connectors 24, 22 overlapping the concave edges 58 of the opposite connectors 22, 24. This overlapping ensures that no gaps are present between the edges of the circumferential elements 14. It is noted that, in some examples, circumferential elements 14 may have a height 20 so that edges 56, 58 do not overlap at the deployed diameters within the vessel treatment range. Alternatively, there may be varying amounts of overlap along the length of the prosthesis 10. Overlap will preferably occur at all deployed diameters within the treatment range. Overlapping of edges at all deployed diameters provides an improved strength uniformity at all deployed diameters as well as increasing crush strength and radial strength of the prosthesis.

Figure 6:
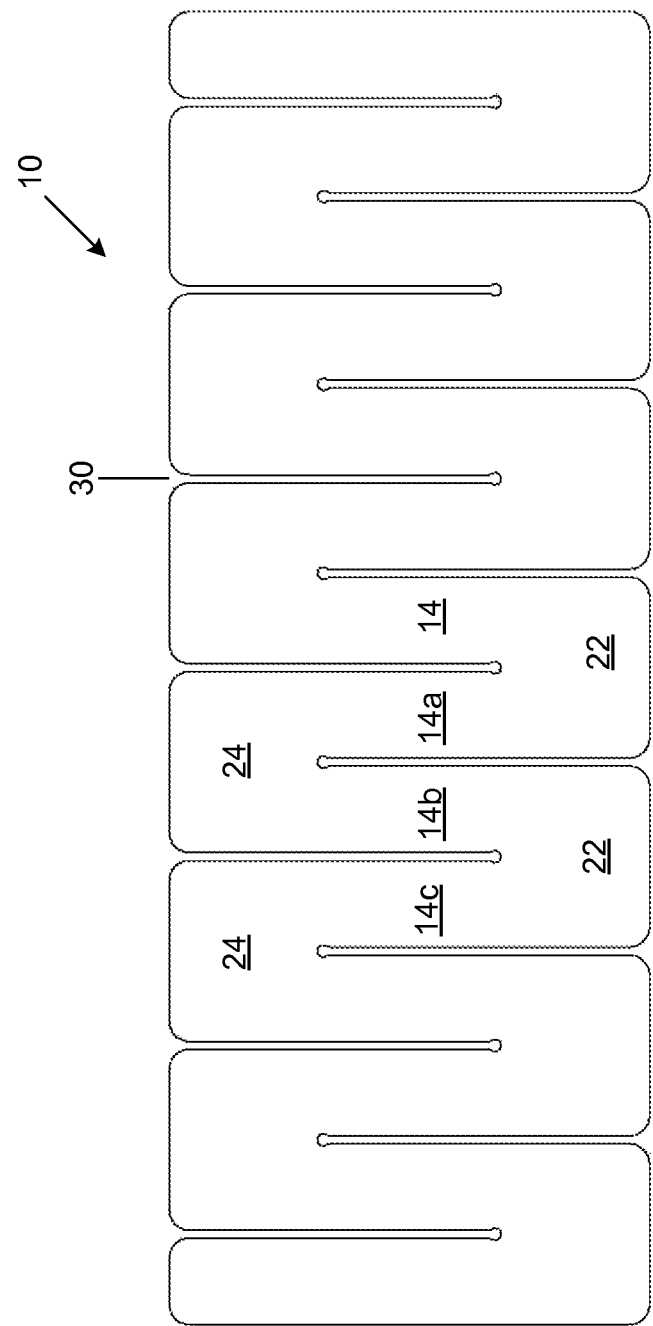
FIG. 6 illustrates an example of a prosthesis in which the circumferential elements are taller than their widths and taller than the connectors.

FIG. 6 is a view similar to that shown in FIG. 5 illustrating an example of a vascular prosthesis 10 having a basic profile with the circumferential elements 14 and the first and second connectors 22, 24 having rectangular shapes. Rectangular shaped circumferential elements maximize the surface area contacting the outer, delivery sheath in its constrained state. This may reduce deployment force by spreading the outward acting force over a larger surface and minimizing the open space between connectors for sheath material to embed into. A rectangular circumferential element also results in a reduced circumferential height. Reduced prosthesis height results in possible smaller constrained diameter and also a lesser unwinding of the prosthesis from constrained diameter to deployed diameter.

Figure 7:
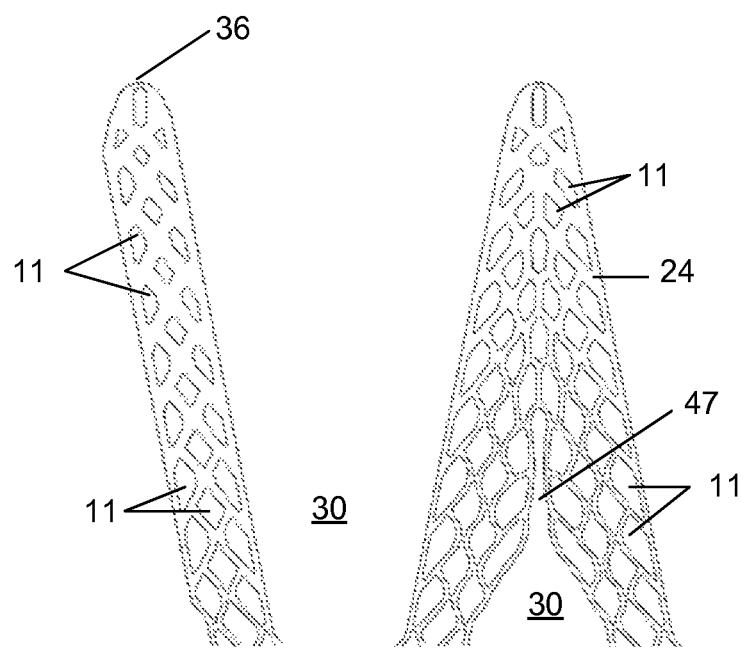
FIGS. 7 and 8 illustrate variations in the pattern of holes along different portions of a prosthesis.
Figure 8:
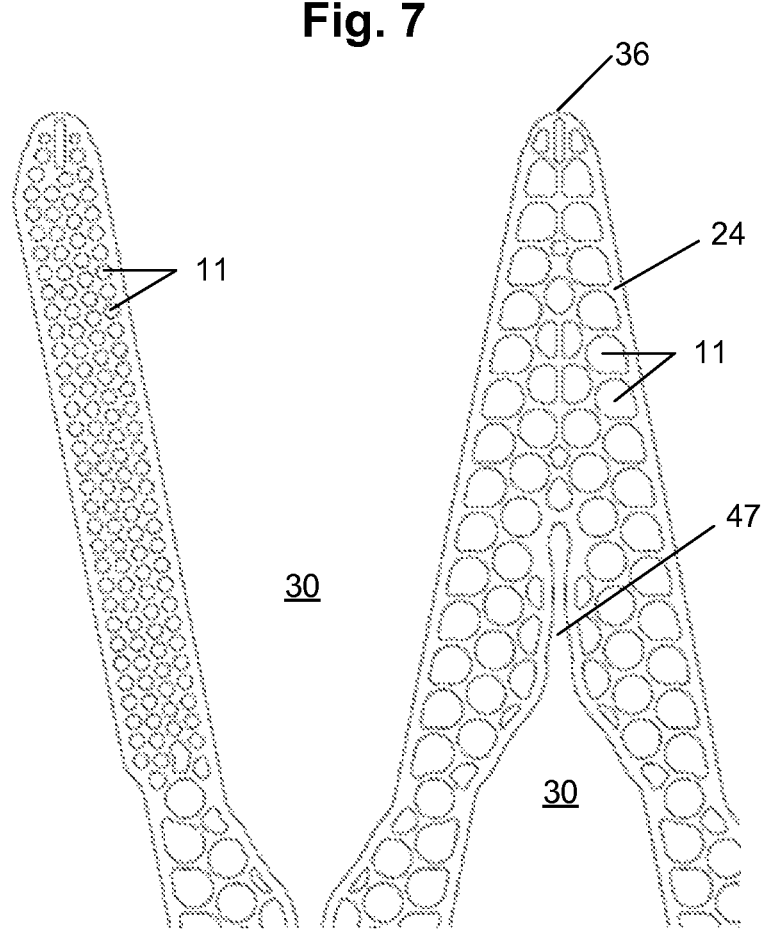

FIG. 7 shows how the choice of the size, shape and spacing for openings 11 can affect the surface area of vascular prosthesis 10. In FIG. 7, the surface area increases from the bottom of the figure, that is towards the center of the circumferential elements, towards the tips 36 of connectors 24. A similar variation could be present towards the tips 36 of connectors 22. FIG. 8 shows a different way of adjusting openings 11 allowing the openings to modify the surface area along selected zones of vascular prosthesis 10 to control properties in the various zones. In addition to affecting the mechanical characteristics of vascular prosthesis 10, variations in the opening 11 can be used to affect the amount and distribution of one or more therapeutic agents housed within the openings. Change to surface area can also be used to control the level of radiopacity of selected prosthesis elements.

Figure 9:
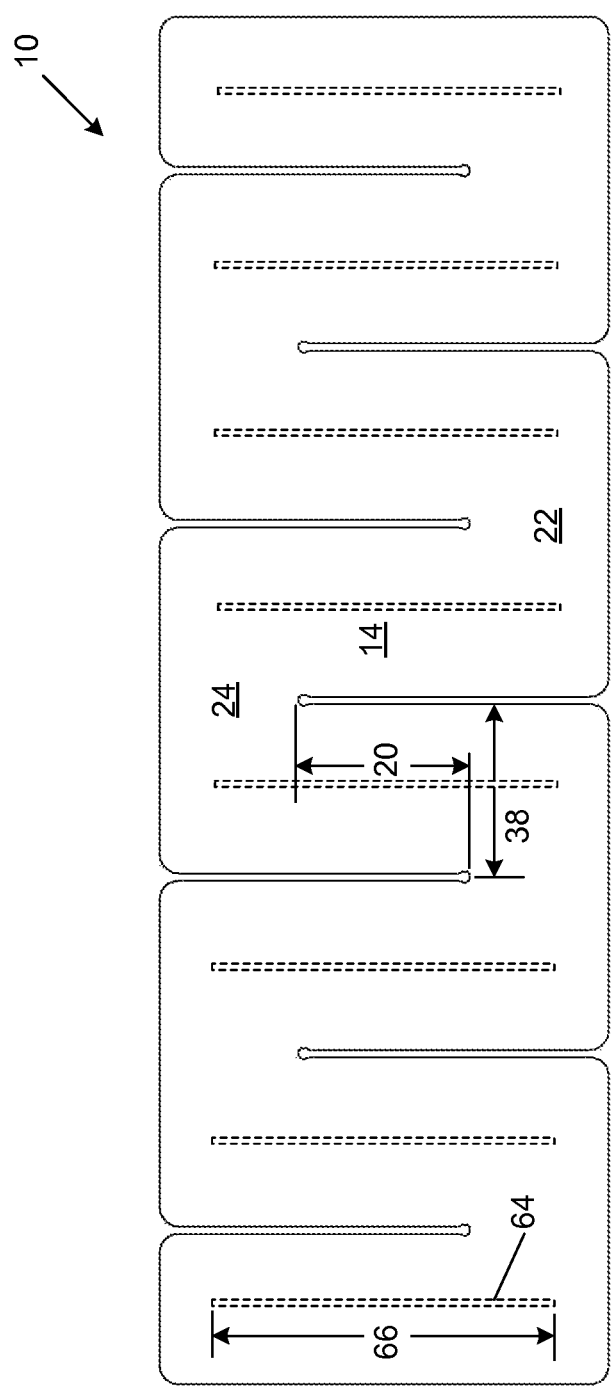
FIG. 9 illustrates an example of a prosthesis in which the circumferential elements are approximately equal in height and width with optional slots located within the circumferential elements to improve prosthesis flexibility.

FIG. 9 depicts another embodiment of vascular prosthesis 10 that has wider circumferential elements 14 in which the height 20 and width 38 are approximately equal (1:1 ratio). This variation decreases the number of circumferential elements 14, potentially increasing radial strength and easing prosthesis delivery and expansion. In FIG. 9, optional slots 64 located within the circumferential elements 14 are present to provide improved prosthesis lateral flexibility. Slots 64 having length 66. Length 66 is preferably more than 50% and less than 95% of the total circumferential length 28.

Figure 10:
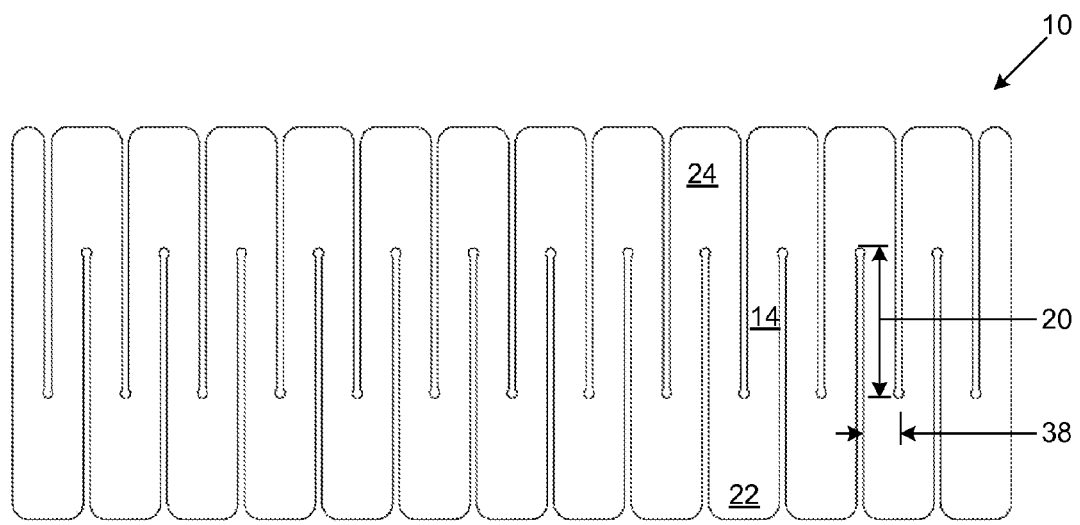
FIG. 10 illustrates an example of a prosthesis in which the circumferential elements are approximately 5 times taller than wide.

FIG. 10 depicts an embodiment where the circumferential elements 14 are narrowed such that they are significantly taller (height 20) than they are wide (width 38), about a 4:1 ratio of height versus width. This variation potentially increases axial, torsional, and bending flexibility, curvature conformability, and the ability of the prosthesis to appose to non-uniform lesion surfaces. This embodiment also increases the flexibility of the prosthesis when constrained in the delivery system to improve deliverability across tortuous vessels.

Figure 11:
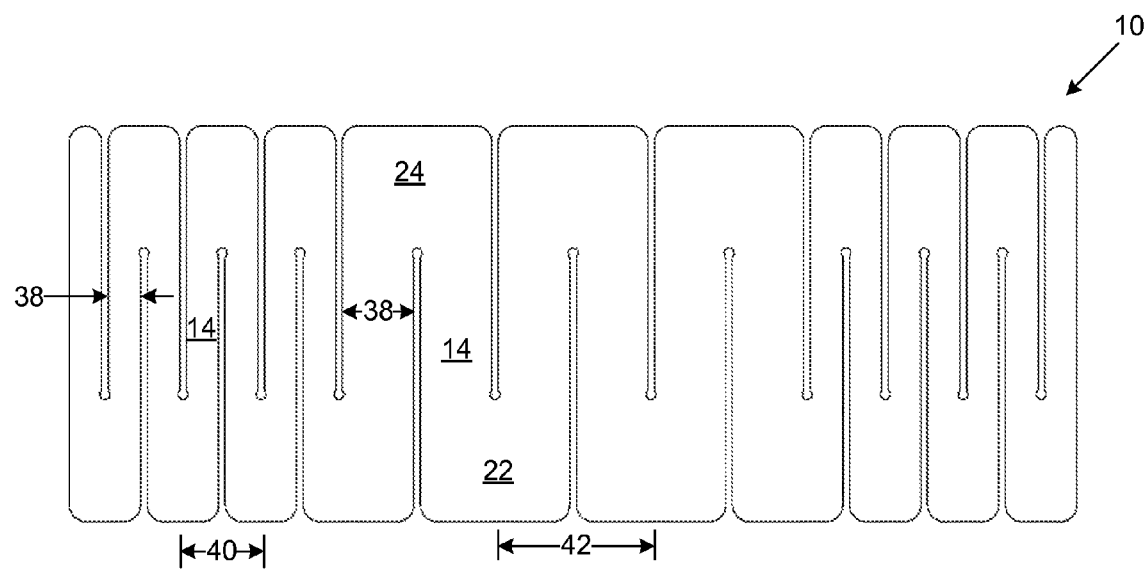
FIG. 11 illustrates an example of a prosthesis in which the widths of the circumferential elements vary along the length of the prosthesis.

FIG. 11 depicts an embodiment wherein the circumferential elements 14 have varying widths 38, with correspondingly varying connector-to-connector distances 40, 42. This variation potentially causes variable flexibility, conformability, and radial strength along the length of vascular prosthesis 10. The presence of narrower circumferential elements 14 at the prosthesis ends, causing greater flexibility and conformability, could have the benefit of serving as a compliance transition zone from native anatomy to the prosthesis. In addition, in the case of stent overlap, the more flexible and weaker ends would be "doubled up," potentially creating more uniform mechanical support for the lumen along the entire treated length of the vessel.

Figure 12:
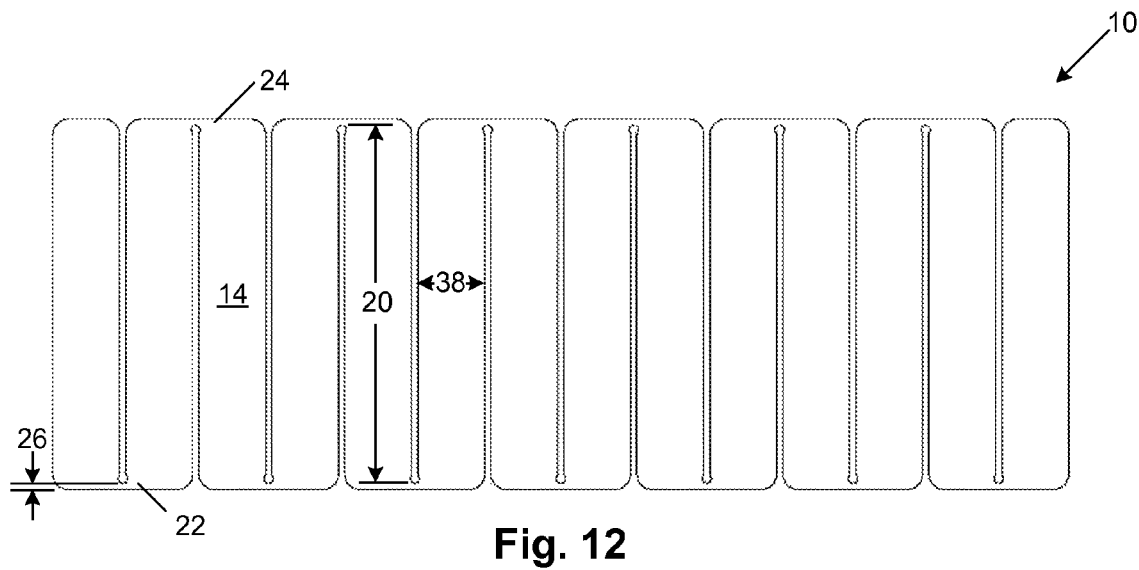
FIG. 12 illustrates an example of a prosthesis in which the lengths of the stress-release slots are almost as long as the total circumferential length of the prosthesis.

FIG. 12 depicts an embodiment where the stress relief slots 30 are extended such that the connectors 22, 24 are very short and the circumferential elements 14 are significantly taller than they are wide (~5:1). This variation increases axial, torsional, and bending flexibility by lengthening the flexing elements in the prosthesis. In a preferred embodiment, the circumferentially-extending connector length 26 would be greater than 10% of the total circumferential length 28, whereby stability and apposition of the device within the vessel is provided. In additional examples, the stress relief slots 30 may be curved or angled relative to the height axis, a vertical axis in FIG. 12, of the prosthesis 10.

Figure 13:
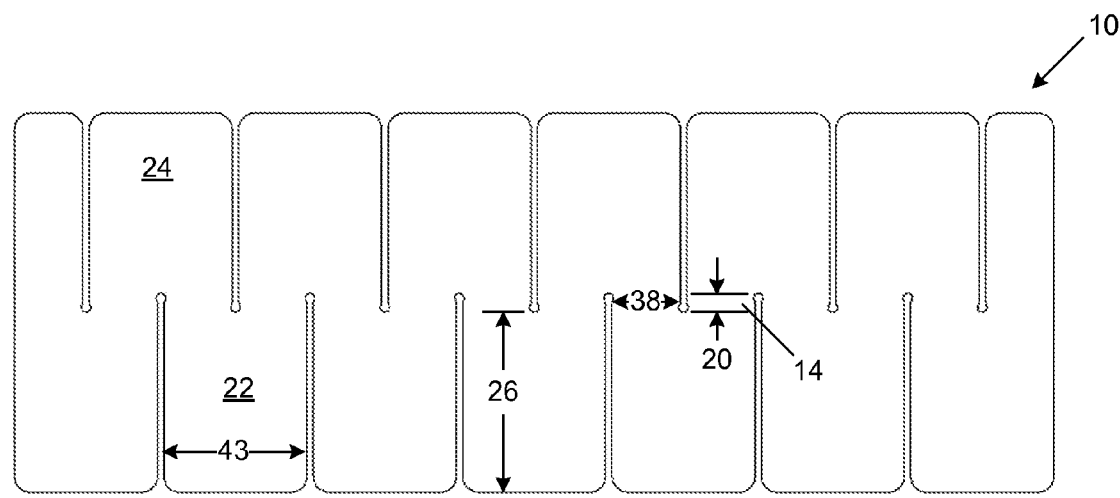
FIG. 13 illustrates an example of a prosthesis in which the lengths of the stress-release slots are just over half the total circumferential length thereby creating short circumferential elements.

FIG. 13 depicts an embodiment where the stress relief slots 30 are shortened such that the circumferential elements are extremely short (~1:7 height 20 to width 38 ratio), leaving connectors as the main elements of the prosthesis (~5:4 height 26 to width 43 ratio). This variation could produce higher radial strength and improve axial stability of the device. Improved axial stability (reduced axial flexibility) can make the device less prone to migration or axial shifting. In a preferred embodiment, the circumferentially-extending connector length 26 would be less than 50% of the total circumferential length 28, thereby eliminating the creation of an axially extending backbone, such as disclosed in the above-referenced U.S. Pat. No. 5,632,771 to Boatman, so that axial flexibility is provided for the body without sacrificing deployment dynamics.

Figure 14:
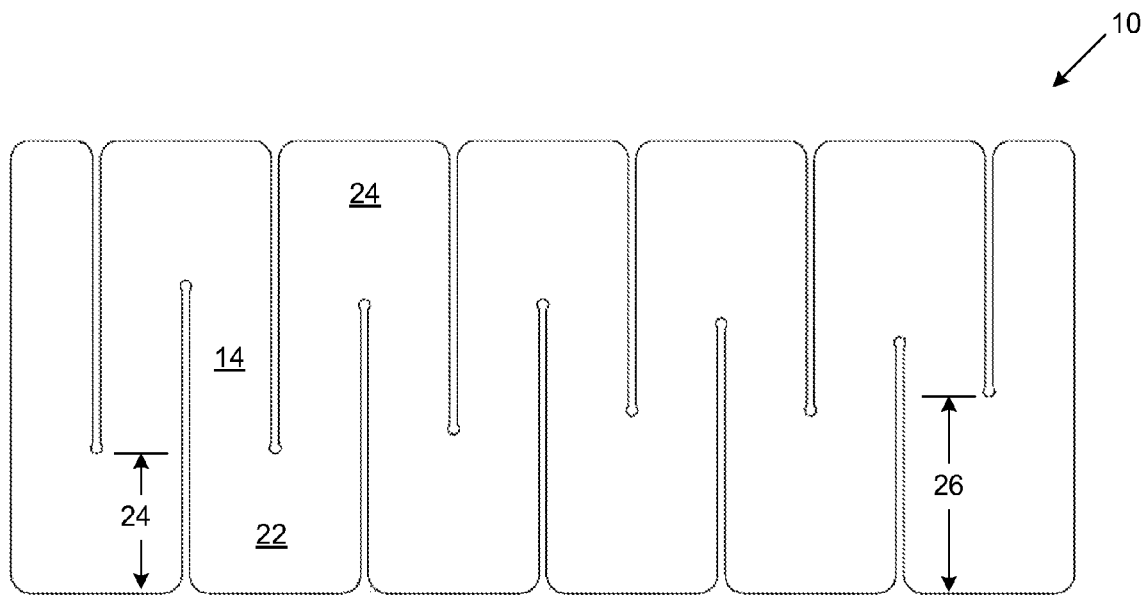
FIG. 14 illustrates an example of a prosthesis in which the lengths of the stress-release slots changes along the length of the prosthesis.

FIG. 14 depicts an embodiment where the lengths 32 of the stress relief slots 30 are variable along the length of the prosthesis, effectively varying the heights 20, 26 of the circumferential and connector elements 14, 22/24. This variation enables variable flexibility, as with the variable width design depicted in FIG. 11.

Figure 15:
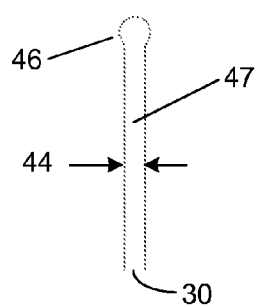
FIG. 15 is an enlarged view of a stress release slot illustrating the keyhole shaped feature at its closed end.

Other features of the stress relief slot 30, as shown in FIG. 15, include the stress relief slot width 44 and the keyhole-shaped feature 46 that extends to a connector 22, 24. The stress relief slot width 44 determines the separation of the circumferential elements 14. Wider stress relief slot widths 44 allow greater separation for a reduced risk of circumferential element overlap during axial compression; doing so may affect features such as vessel scaffolding and surface area coverage. The keyhole-shaped feature 46 provides localized stress relief, distributing the load within the adjacent connector 22, 24. As in the case of other stress relief slot features, the keyhole-shaped design may have various sizes and shapes, as appropriate for the macrostructure of the prosthesis design and the biomechanical loads of the intended treatment anatomy.

In some examples, the body 12 in the region surrounding the curved closed ends at the keyhole shaped feature 46 of the stress relief slots 30 has higher surface areas than the average surface area for the rest of the body for strength. Keyhole shaped feature 46 has a lateral dimension. In some examples, body 12 in the region adjacent to feature 46 is substantially free of holes for a distance equal to the lateral dimension, thereby reducing stress concentrations and gaining strength. Strength is also enhanced in some examples because the body in the region adjacent to the narrow width portion 47, including the keyhole shaped feature 46, is substantially free of holes for at least 0.25 mm.

The stress relief slots 30 preferably have narrow width portions 47 over a majority of the relief slot lengths. The narrow width portions have lateral dimensions, that is widths 44, of no greater than about 3 mm (0.120 inch). In some examples, width 44 is between about 0.13 mm (0.005 inch)

and 1 mm (0.040 inch). A width 44 of less than 0.5 mm (0.020 inch) is presently preferred. The relatively narrow width of narrow width portions 47 helps to minimize the gaps between the circumferential portions 14 thereby helping to reduce tissue prolapses and create better tissue coverage at the target site. In many of the examples, narrow width portions 47 have a generally constant width, such as in FIGS. 3-5, while the other examples, such as in FIGS. 7 and 8, the narrow width portions have a variable width. The variable width portions 47 may be, for example, smoothly curving, as shown, or a stepped configuration or a combination thereof.

Figure 16:
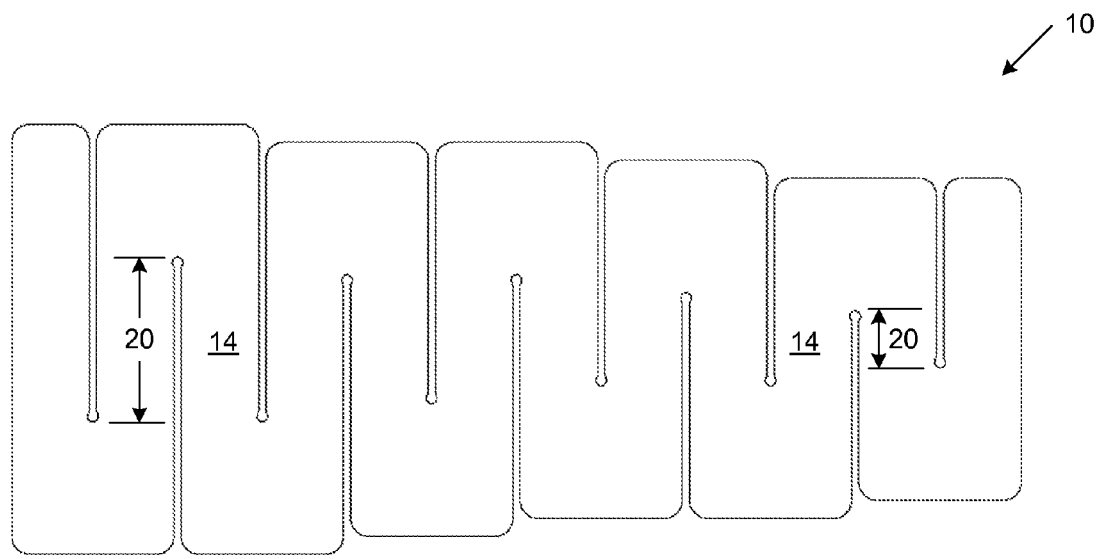
FIG. 16 illustrates an example of a prosthesis in which the heights of the circumferential elements change along the length of the prosthesis.

FIG. 16 depicts an embodiment wherein the height 20 of the circumferential elements 14 varies along the length of the prosthesis 10. Since the height 20 of the circumferential element 14 is typically directly related to the diameter of the generally tubular vascular prosthesis 10 at that location, a shorter circumferential element translates to a smaller diameter ring. This variation has a height-to-width ratio of ~2:1 at the tall end and transitions down to a ratio of ~3:4 at the short end, in this example. This tapering-diameter prosthesis may be appropriate for implantation into a tapered lumen as frequently occurs over longer lengths of vessels. Although not shown, by varying the connector length 20 and maintaining a longer stress relief slot length 32 than shown in FIG. 16, improved flexibility may be achieved.

Figure 17:
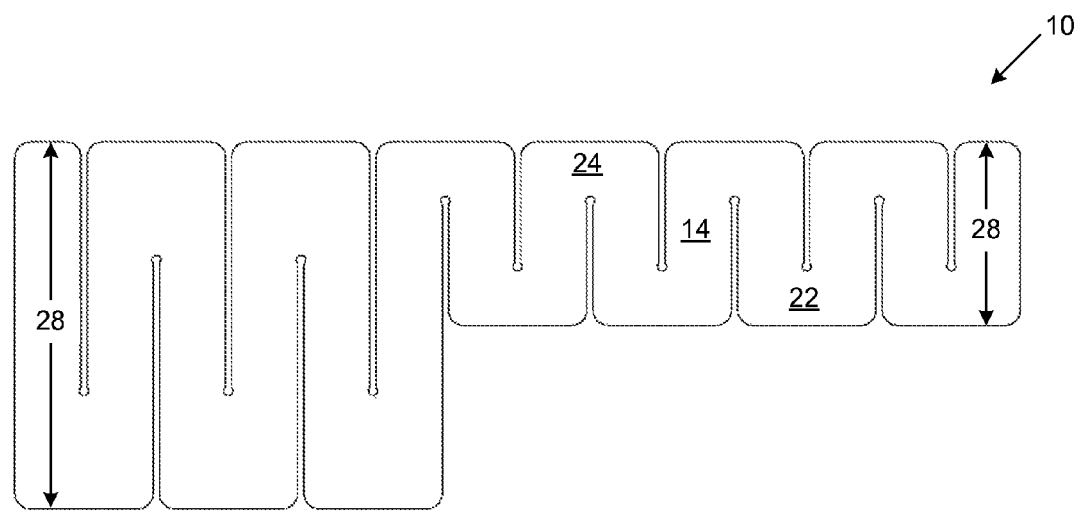
FIG. 17 illustrates an example of a prosthesis in which the height of the connectors and the circumferential elements are abruptly changed along the length of the prosthesis.

FIG. 17 depicts an embodiment where the heights 20 and 26 of the circumferential elements 14 and the connector elements 22, 24 transition abruptly at a certain point along the length of the prosthesis 10. On the tall side, the left side in the figure of this example, the height 28 of the prosthesis portion is twice that of the height of the prosthesis portion on the short side. This means that the prosthesis 10 will have two distinct diameters, which may be ideal for treating within a lumen with a branching, smaller lumen.

Figure 18:
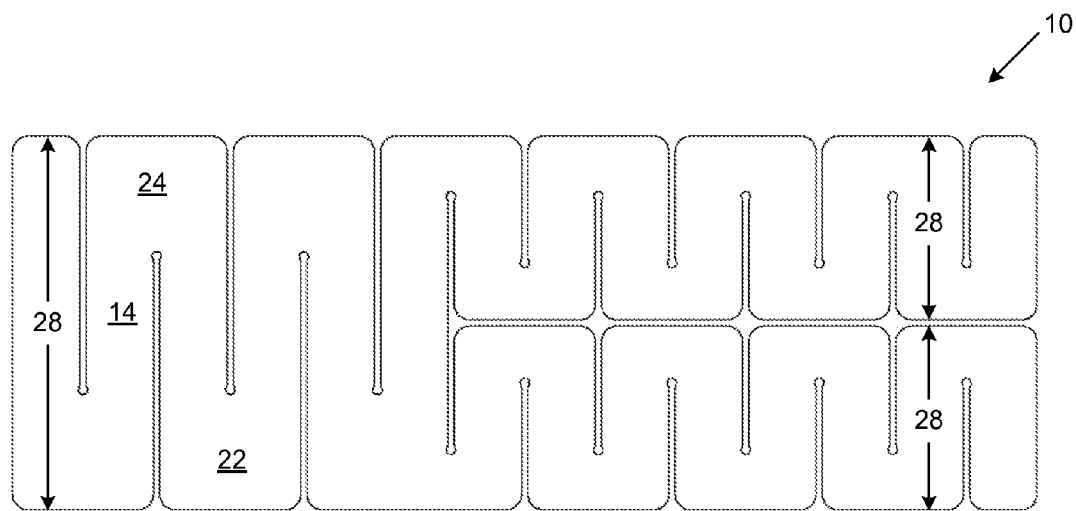
FIG. 18 illustrates an example of a prosthesis in which the height of the connectors and circumferential elements abruptly bifurcate into two independent prosthesis portions.

FIG. 18 depicts an embodiment where the heights 20 and 26 of the circumferential elements 14 and the connector elements 22, 24 abruptly bifurcate into two independent lengths of stent, also sometimes called prosthesis portions. In this example, on the non-bifurcated prosthesis portion, the height 28 is twice that of an individual bifurcated prosthesis portion. Both of these bifurcated portions are connected by a connector element 22, 24 to the non-bifurcated portion. This means that the prosthesis can have multiple distinct diameters, with two bifurcated prosthesis portions branching off from the main prosthesis portion. This may be ideal for treating a lumen with two branching, smaller lumens. This concept can further be applied to vessels with more than two branches, including a vessel with as many branches as stent geometry allows. Also, the height 28 of each prosthesis portion on the short side can be different from one another.

Figure 19:
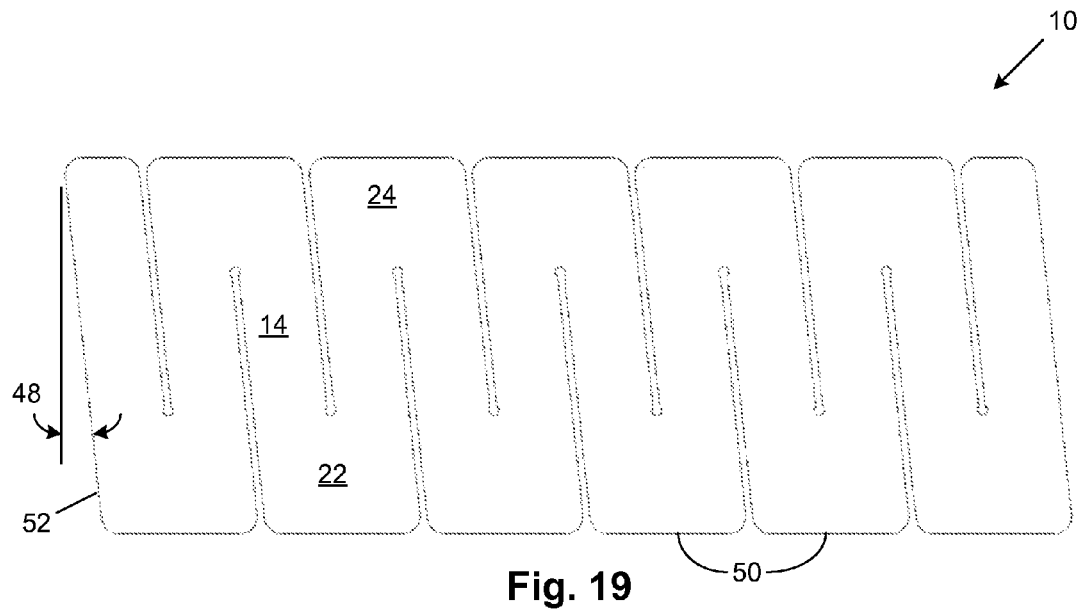
FIG. 19 illustrates an example of a prosthesis in which the edges of the circumferential elements are angled, that is not perpendicular, to the axis of the prosthesis.
Figure 20:
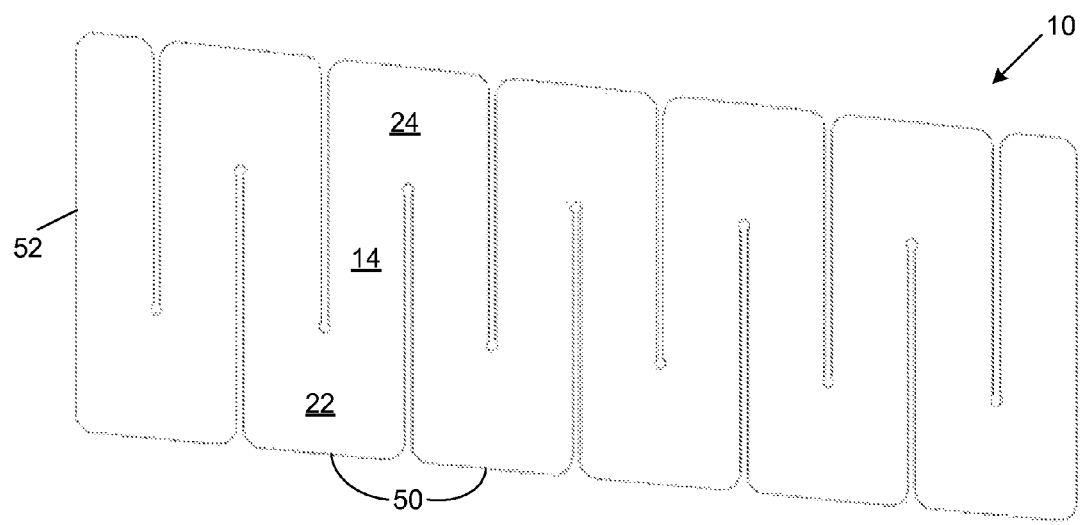
FIG. 20 illustrates an example of a prosthesis in which the edges of the circumferential elements are perpendicular to the axis of the prosthesis while the longitudinal edges created by the connectors are at an angle, that is not parallel, to the axis of the prosthesis.

FIGS. 19 and 20 depict an embodiment where the prosthesis 10 is slanted at an angle 48 across the length. This angle 48, depicted in these examples as 6.1°, provides longitudinal flexibility in conjunction with the stress relief slot features without sacrificing radial strength. The angle may be increased to provide additional longitudinal flexibility. An increased angle will also limit the circumferential stiffness discontinuity associated with a longitudinally-oriented overlap in the deployed configuration. This prosthesis 10 may be wrapped down on an axis parallel to one longitudinal edge 50 of the prosthesis as depicted in FIG. 19. Alternately, the prosthesis 10 may be wrapped down on an axis angled to the longitudinal edge 50 of the prosthesis 10 as depicted in FIG. 20, typically perpendicular to edge 52, thereby maintaining the circumferential elements perpendicular to the axis of the vessel.

Figure 21:
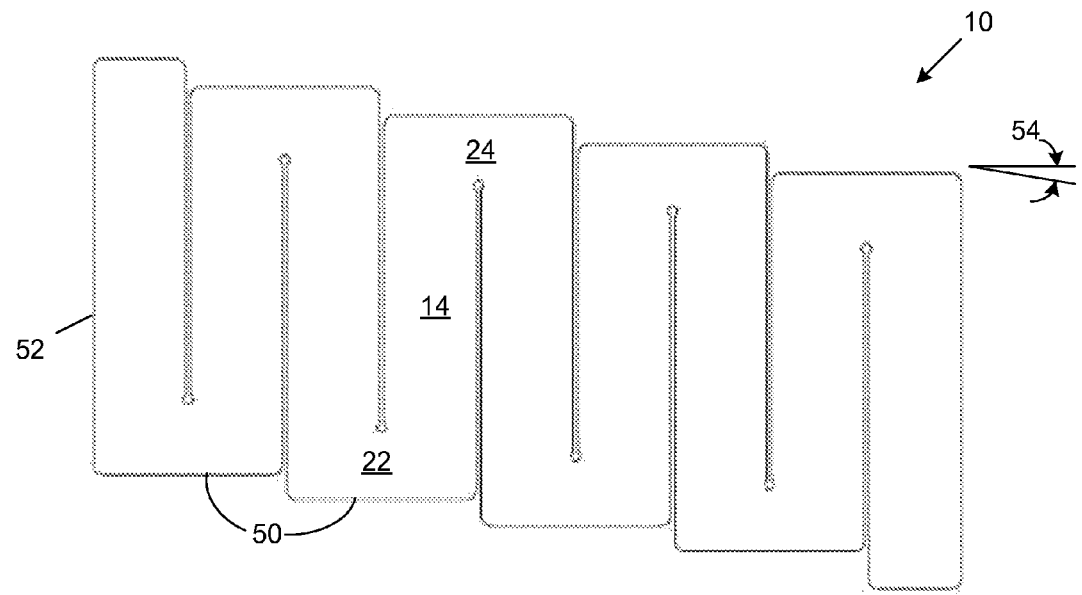
FIG. 21 illustrates an example of a prosthesis in which the height of the circumferential elements are changed along the length of the prosthesis to create a step pattern to the longitudinal edges.

FIG. 21 depicts an embodiment where the prosthesis 10 creates a step pattern at an angle 54 along the stent length. The angle 54, depicted in this example as 7.5°, limits the circumferential stiffness discontinuity along the stent length associated with a longitudinally-oriented overlap in the deployed configuration. The prosthesis 10 may be wrapped down on an axis parallel to one stepped longitudinal edge 50 of the stent as depicted in FIG. 21, thereby maintaining the circumferential elements 14 perpendicular to the axis of the vessel. Alternately, the prosthesis may be wrapped down on an axis angled to the longitudinal edge of the stent, such as perpendicular to edge 52, thereby creating circumferential elements 14 angled to the axis of the vessel.

Figure 22:
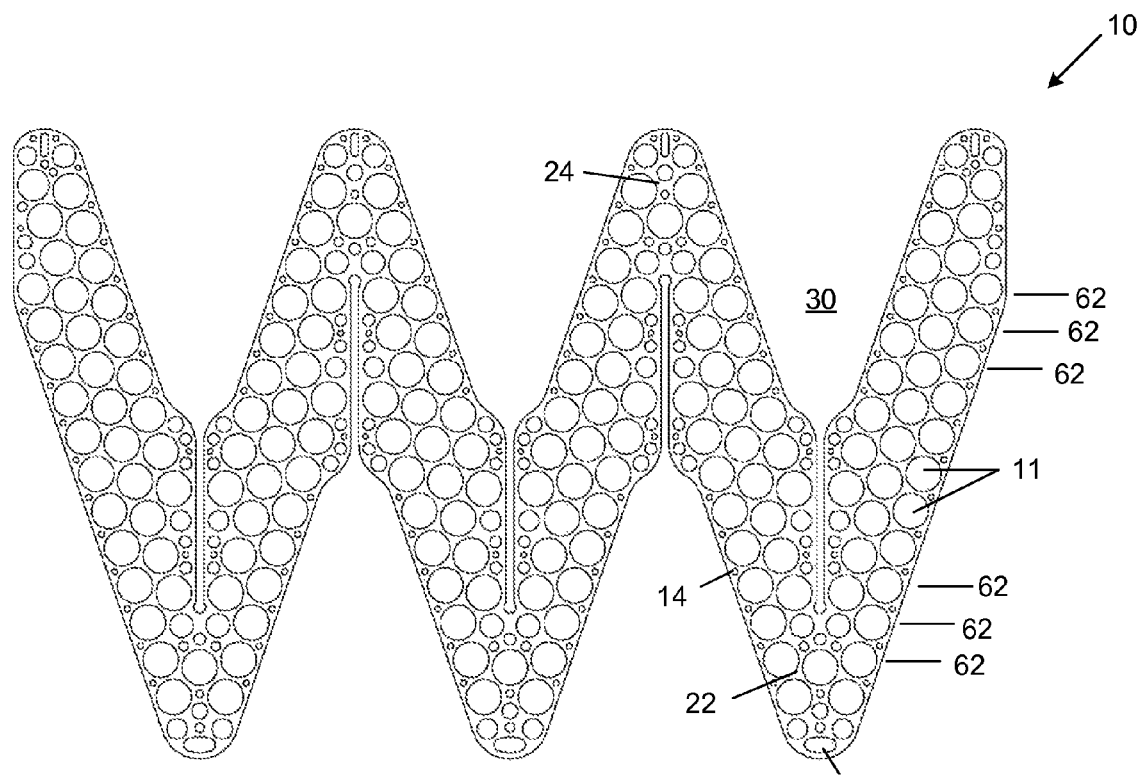
FIG. 22 illustrates an example of a prosthesis in which the connectors are generally triangular in shape, and the circumferential elements have non-parallel portions.

FIG. 22 depicts a complete two-dimensional design of one example of vascular prosthesis 10, similar to the examples illustrated in FIGS. 3 and 4, where the circumferential elements 14 are not rectangular with a height 20 to width 38 ratio of about 1:2, and the alternating connectors 22, 24 are generally triangular in shape. This design reduces the potential gap when the prosthesis 10 is at its largest treatment diameter and the apex or tip 36 of connectors 22, 24 do not overlap with the mating edges. This design also limits the circumferential stiffness discontinuity associated with a longitudinally-oriented overlap in the deployed configuration. Further, this design decreases the surface area of the prosthesis 10 in contact with the outer sheath (not shown) in the constrained state, which may reduce deployment forces in scenarios where embedding into the outer sheath material is a concern. The design shows a pattern of circles that determines the metal area percentage of the prosthesis, which in this case is ~35% metal coverage. Higher metal percentages potentially provide more drug loading capacities and radiopacity, while also radially strengthening the prosthesis. Lower metal percentages potentially enable better branch perfusion, faster healing, and greater flexibility.

Figure 23:
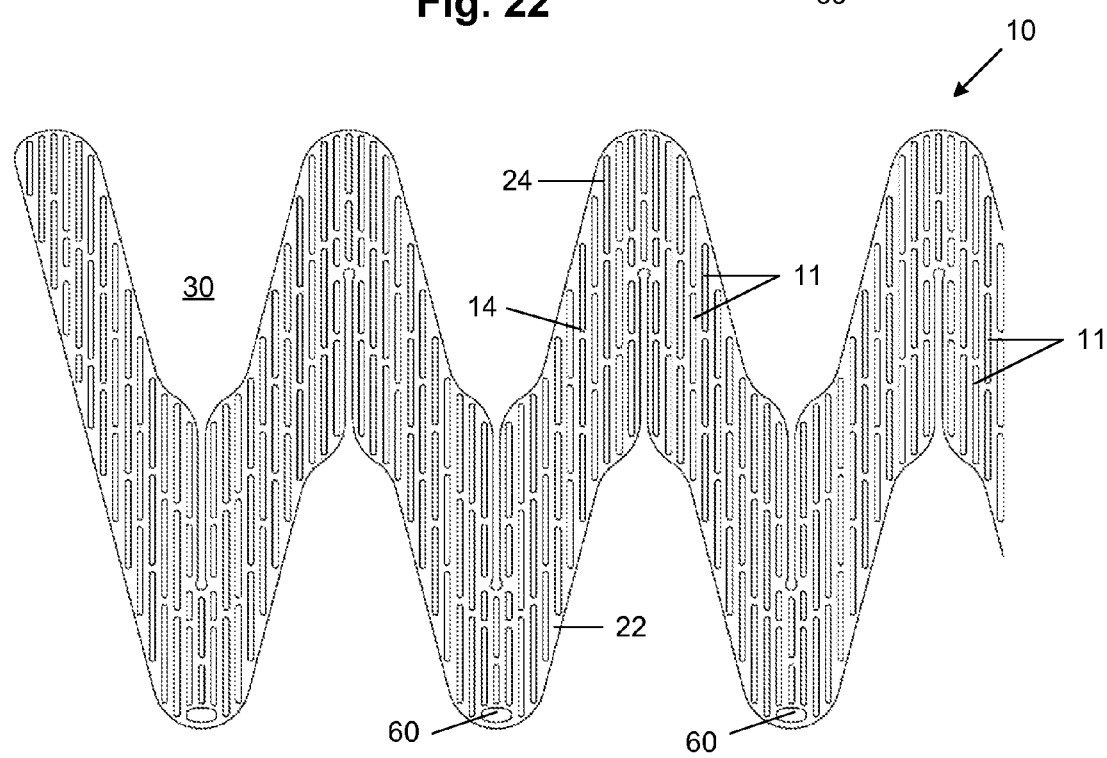
FIG. 23 illustrates an example of a prosthesis in which the opening are circumferentially extending slots instead of round holes.

FIG. 23 depicts a design for vascular prosthesis 10 in which the internal features 11, typically referred to as openings 11 or holes 11, are slots in the circumferential direction of the prosthesis, providing metal area coverage of ~60%. This design effectively provides hinge points for flexing the prosthesis in the axial direction. First, this may provide greater conformability of the prosthesis to the vessel after implant. Second, the flexibility of the prosthesis may enable easier restraint of the prosthesis in the delivery system via enhanced nesting (wrapped layer-to-layer intermingling) when the prosthesis is wrapped. Third, the prosthesis may provide more longitudinal flexibility when wound down and constrained in the delivery system.

FIG. 3 depicts a design in which the circumferential elements 14 are taller, height 20, than they are wide, width 38, by about a 2:1 ratio. The alternating connectors 22, 24 are generally triangular in shape, the connector-to-connector distance 40 is decreased as compared to FIGS. 22 and 23, and the prosthesis height 28 is decreased as compared to FIGS. 22 and 23. In addition, the internal pattern of openings 11 produces a metal area percentage of about 50%. The shortened connector-to-connector distance 40 provides enhanced curvature conformability. The shortened height 28 of the prosthesis 10 enables the prosthesis to be constrained with fewer wraps in the deployment system, potentially improving expansion force and consistency during deployment.

Figure 24:
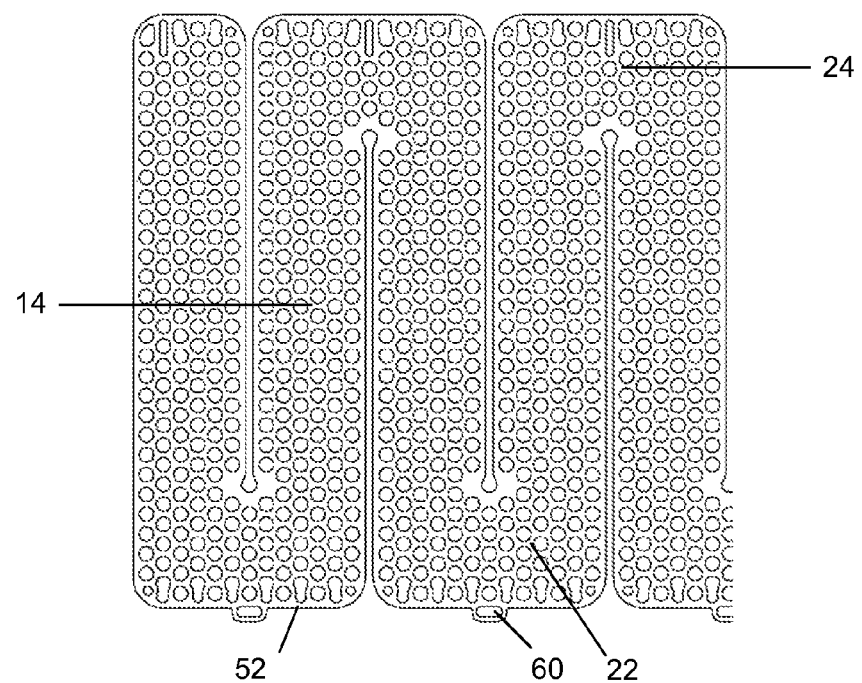
FIG. 24 illustrates an example of a prosthesis in which engagement openings are provided by a small, flexible loop along one lateral edge to aid in wrapping the prosthesis to the contracted state.

FIG. 24 depicts a design for prosthesis 10 in which engagement openings 60, in the form of small, flexible loops 60 on the connectors 22, aid in capturing the stent during wrapping into its constrained state.

Figure 24A:
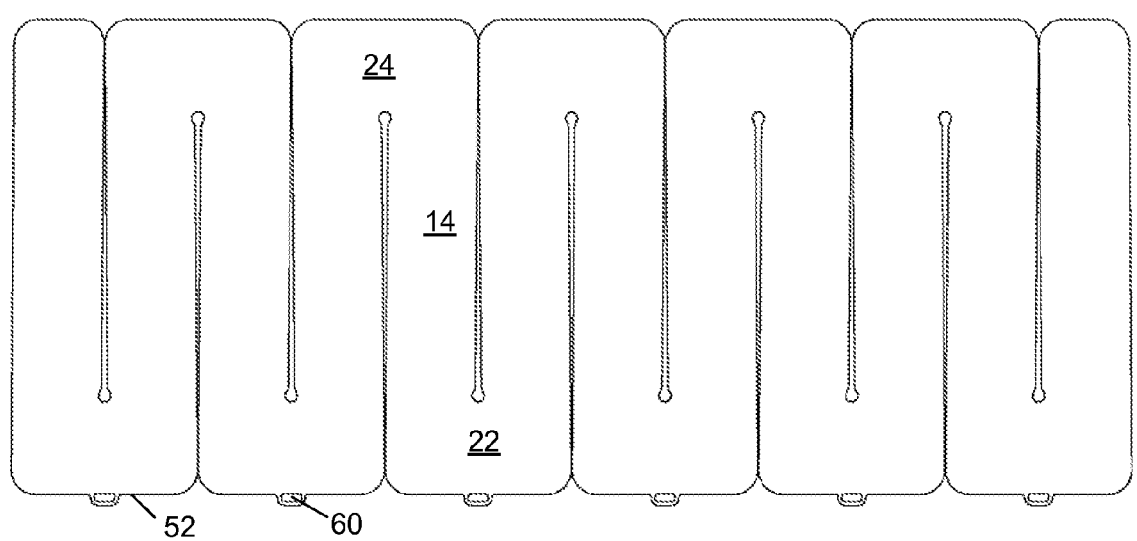
FIG. 24A illustrates an example of the prosthesis of FIG. 24 in which the gap between the circumferential elements is pre-compressed, the method intended for use while the prosthesis is in the wrapped state within the delivery system, but is presented in flattened form for visual clarity.

FIG. 24A depicts a method in which the prosthesis from FIG. 24 is compressed after loading the prosthesis into the delivery system. After prosthesis is initially loaded into the delivery system, the prosthesis is compressed axially to collapse the gap between adjacent circumferential elements 14. In such a pre-compressed state, the loaded prosthesis will have optimal layer-to-layer alignment and axial stiffness during final stent deployment. The alignment and stiffness are particularly important to maintain when high deployment forces are required. Since the act of delivery sheath retraction may cause axial shifting of circumferential elements, full axial compression of the stent prior to delivery further improves stent length control and predictability by removing compression variability.

Figure 25:
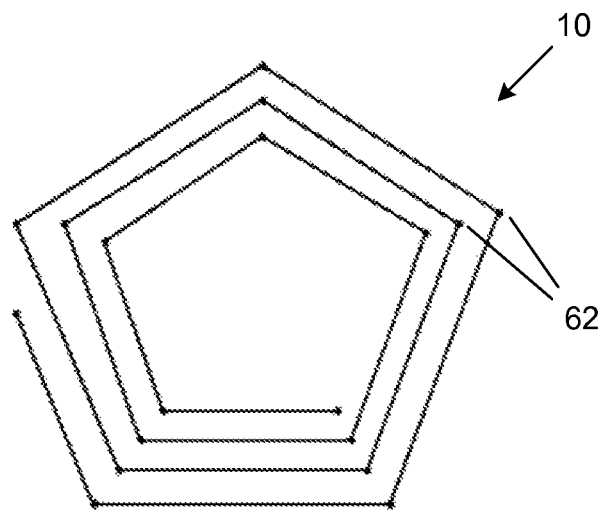
FIG. 25 illustrates, in a schematic and exaggerated form, an end view of an example of a prosthesis in a contracted state showing how hinge points can align so that the facets interlock to a certain extent thus reducing the amount of radial force exerted by the prosthesis on the delivery sheath.

Referring again to vascular prosthesis 10 shown in FIG. 22, the concept of hinge points will be discussed. When a prosthesis 10 is wrapped down to a constricted, delivery state, the resistance to this wrapping down is not constant. That is, certain regions of the vascular prosthesis 10 are less stiff than other regions. The variation in stiffness is primarily due to the amount of material being wound down. The amount of material is typically affected by the size and spacing of openings 11 and the thickness of the material. The variation in stiffness creates hinge points 62, at which the device is more flexible, that are less resistant to being wound down than adjacent portions of the device. When wound down, the cross-sectional shape is therefore not completely smooth. FIG. 25 illustrates, in a schematic and exaggerated form, how these hinge points 62 create facets which may be aligned in the constricted, delivery state. Such alignment may cause the different layers of vascular prosthesis 10 to interlock to a certain extent thus reducing the amount of radial force exerted on the delivery sheath and resulting embedding into the sheath. Reducing the amount of radial force exerted on the delivery sheath, which can reduce the amount the vascular prosthesis 10 becomes embedded into the inner wall of the delivery sheath, can help reduce the amount of force necessary to remove vascular prosthesis 10 from the delivery sheath. Instead of hinge points, a self expanding vascular prosthesis 10 could include other features that engage when the prosthesis is wound down to a delivery state so to inhibit the unwinding of the vascular prosthesis thereby reducing the amount of force exerted by the prosthesis on the inner wall of the delivery sheath. For example, vascular prosthesis 10 could include complementary raised portions and recesses that become aligned in the delivery state. Also, vascular prosthesis 10 could have radially outwardly extending features that engage overlying portions of the vascular prosthesis when in the delivery state. In any event, when vascular prosthesis 10 begins unwinding and radially expanding upon release from the delivery sheath, such engagement features would release or otherwise disengage permitting the essentially free expansion of the vascular prosthesis.

Figure 26:
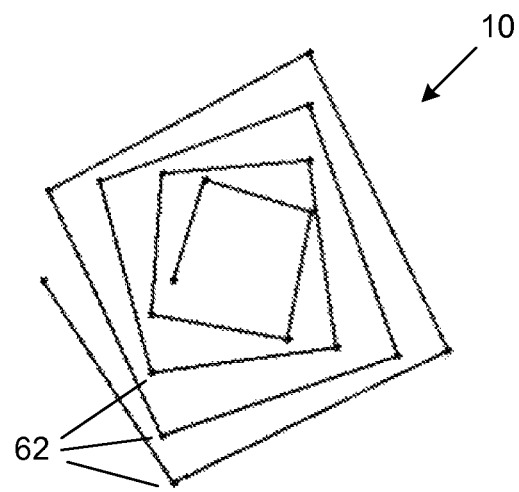
FIG. 26 illustrates, in a schematic and exaggerated form, an end view of an example of a prosthesis in a contracted state showing how hinge points can be misaligned so that the facets do not interlock to minimize contact of stent layers or to improve the ability of circumferential elements to axially stabilize each other during delivery sheath removal.

FIG. 26 illustrates, also in a schematic and exaggerated form, how the vascular prosthesis 10 can be constructed so that hinge points 62 are not aligned in the constricted, delivery state thus minimizing interlock and contact of stent layers. If the prosthesis is coated with drugs or other coating material, this configuration can limit contact with the coating and the potential damage from contact. Also, this configuration can improve the ability of circumferential elements to contact and axially stabilize each other when a delivery sheath is removed (reducing likelihood of axial shifting). Vascular prosthesis 10 can be designed so that hinge points 62 are or are not created when the prosthesis is placed in a contracted state. If hinge points 62 are desired, the locations of the hinge points can be influenced by, for example, the location, size, and shape of openings 11.

It is a further feature of some examples of the present invention to provide apparatuses and methods for a prosthesis that exhibits a low profile when implanted into the body lumen. The low profile prevents disruption of blood flow and avoids adverse hemodynamic conditions known to be correlated with flow recirculation and thrombosis. The low profile is preferably achieved by the use of a very thin geometry that is lower profile than traditional slotted-tube designs when deployed at the treatment diameters, even in the presence of overlapped regions of the prosthesis.

It is a further feature of some examples of the present invention to provide apparatuses and methods for a prosthesis that exhibits a low profile in a constrained state inside the delivery system. The low profile is achieved by the use of a very thin cross-sectional geometry with a minimal number of overlaps in the constrained state.

It is a further feature of some examples of the present invention to provide apparatuses and methods for a prosthesis that exhibits minimal foreshortening from its length in the delivery system and its deployed length. This is achieved by the prosthesis deploying with an unwinding action, from a radially contracted state, to a more relaxed, radially expanded deployed state.

It is a further feature of some examples of the present invention to provide apparatuses and methods for a prosthesis that exhibits sufficient flexibility to conform to the natural shape of the body lumen without causing trauma or substantially remodeling the anatomy. This flexibility also enables ease of delivery of the prosthesis and provides the ability for long-term survival of the prosthesis within the body without fatigue and fracture. The prosthesis exhibits a design by using a stress relief slot 30 that dampens stresses associated with repetitive axial (tension and compression), torsional, and bending loads.

It is a further feature of some examples of the present invention to provide apparatuses and methods for a prosthesis that simultaneously exhibits high radial resistance to compression along with the high levels of axial, torsional, and bending flexibility mentioned above. The circumferential and connector elements 14, 22, 24 of the prosthesis naturally provide radial strength, while the alternating connection of a plurality of these circumferential elements provides flexibility in other directions.

It is a further feature of some examples of the present invention to provide apparatuses and methods for a prosthesis that contains circumferential elements 14 designed such that they deploy from a constrained state to an expanded state in the body lumen in a safe and reliable manner with sufficient outward force to obtain full apposition to the lumen. In addition, once deployed, the prosthesis has the ability to be expanded further by balloon inflation (in the lumen of the prosthesis) if the prosthesis did not obtain full apposition to the vessel. To achieve both of these goals, the prosthesis "height" is reduced (preferably less than 2× the circumference of the maximum lumen size such that the number of wrapped layers is limited, hence easing the action of prosthesis unwinding.

It is a further feature of some examples of the present invention to provide apparatuses and methods for a prosthesis that has a small delivery configuration (in the constrained, radially contracted state) to enable the prosthesis to be delivered into smaller body lumens. This goal is also achieved by a short prosthesis "height" (less than 2× the circumference of the maximum lumen size is recommended, but not required), which limits the number of wrapped layers that the prosthesis exhibits while in its constrained state in the delivery system. Once guided to the implant location, the method of constraint is released and the prosthesis expands to its implanted, radially expanded state. The prosthesis may expand to the treatment diameter via multiple mechanisms including, but not limited to, the spring force of the prosthesis exhibiting elastic recovery, the uncoiling of a shape-memory alloy, or the expansion facilitated by a balloon.

It is a further feature of some examples of the present invention to provide apparatuses and methods for a prosthesis that exhibits sufficient surface area to effectively scaffold the treated lumen, provide adequate radiopacity during fluoroscopy, as well as deliver therapeutic agents with adequate spatial distribution and total dosage. The design will also enable enough surface porosity to allow branch flow if so desired. Surface areas in the range of 30% metal up to 85% metal are considered advantageous to the design, although lower or higher metal coverage may be beneficial in some applications.

It is a further feature of some examples of the present invention to provide apparatuses and methods for a prosthesis that has various diameters and lengths that can be prescribed to treat a wide variety of lumen shapes and sizes. The invention may also be configured for tapered (see FIG. 16) or bifurcated (see FIGS. 17 and 18) vessel geometries by providing multiple diameters or tapering diameters along the length of the prosthesis.

It is a further feature of some examples of the present invention to provide apparatuses and methods for a prosthesis that has retention features, such as engagement openings 60, to assist in the process of diametrically reducing the prosthesis within the catheter shaft.

It is a further feature of some examples of the present invention to provide apparatuses and methods for a prosthesis that has features to better distribute the outer acting force against the catheter outer sheath.

It is a further feature of some examples of the present invention to provide apparatuses and methods for a prosthesis that has a micropattern of openings 11 creating hinge points 62 which decreases the outward acting force against the outer sheath. The hinge points 62 may create facets radially such that the facets interlock when constrained in an outer sheath.

It is a further feature of some examples of the present invention to provide apparatuses and methods for a prosthesis that has various methods of fabrication including, but not limited to, laser cutting, stamping, photoetching, or any combination thereof. In addition, the prosthesis may be fabricated from raw stock including, but not limited to, solid tubing or flat sheet.

In a preferred embodiment, the prosthesis comprises a super-elastic material, such as Nitinol, and includes at least two connected circumferential elements 14. However, it should be appreciated that the prosthesis may be constructed from any suitable material recognized in the art, including polymers and biodegradable materials. With more than two circumferential elements 14, the elements are joined by alternating connectors 22, 24 that form a serpentine pattern (FIGS. 3-5). The circumferential elements 14 may be connected as part of the same raw material, or alternative ways including, but not limited to soldering, welding, and/or mechanical features (e.g. rivets). The circumferential and connecting elements can have varied shapes and sizes, with FIG. 6 depicting circumferential elements 14 taller than they are wide (~2:1 ratio), and circumferential elements that are taller than the connectors 22, 24 (~5:4 ratio). The circumferential elements 14 in FIG. 6 are rectangular, which maximizes the surface area contacting the outer, delivery sheath (not shown) in its constrained state. This may reduce deployment force by spreading the outward acting force over a larger surface and minimizing the open space between connectors 22, 24 for sheath material to embed into. A rectangular circumferential element also results in a reduced circumferential height. Reduced prosthesis height results in possible smaller constrained diameter and also a lesser unwinding of the prosthesis from constrained diameter to deployed diameter.

In a preferred embodiment, the body of the prosthesis may be comprised of various features and designs. The geometry, quantity, size, and location of features that comprise the openings 11 within the body largely determine the scaffolding surface area of coverage, radial strength, side branch flow, and spatial drug distribution of the prosthesis. In addition, the pattern of openings 11 need not be symmetric or repeated across the prosthesis. FIGS. 7 and 8 depict examples of prostheses with variable surface area along its height, in which the tips have a higher relative surface area density than lower regions. Varying surface area density may accommodate varying radial or longitudinal requirements for force and flexibility, scaffolding area, drug delivery area, radiopacity, or any combination thereof. A portion or all of the body may also incorporate a full area covering. Additional features including, but not limited to, marker bands may be incorporated in the body. The features may also be specifically designed as drug reservoirs to accommodate drug deposition coating methods.

It will be appreciated that different therapeutic agent delivery modalities may be used in conjunction with the vascular prosthesis of the present invention. For example, vascular prosthesis may include openings 11 in the form of one or more dimples, reservoirs, and/or through-holes that may have a therapeutic agent disposed therein. A therapeutic agent may be incorporated into any of the openings aforementioned, either filling or partially filling the openings. As a still further alternative, a therapeutic agent may be disposed in a matrix coated on any portion of the vascular prosthesis, and the drug may be gradually released into a localized region of a vessel wall. The matrix of coating may include, but is not limited to biostable polymers, biodegradable polymers, ceramics, or metals.

One or more of the prosthesis portions also may be selectively coated with a polymer, such as polyurethane or PTFE. The polymer may partially or fully cover the selected portions. For example, the polymer may be disposed on the circumferential elements 14 to reduce blood flow into a sac of the aneurysm. Additionally, a therapeutic agent may be disposed on the polymer to increase the working surface area.

The therapeutic agents may include, but are not limited to, antiplatelet drugs, antiproliferative drugs, anticoagulant drugs, agents used for purposes of providing gene therapy to a target region, or any combination of therapeutic agents. These therapeutic agents may be tailored for a particular application. Radiopaque markers (not shown) also may be selectively disposed on any portion of the vascular prosthesis in the vicinity of the therapeutic agents to facilitate alignment of the therapeutic agents with a target site on a vessel wall. Advantageously, higher doses of such agents may be provided using the vascular prosthesis of the present invention, relative to previously known coils or stents having interconnected struts, due to the increased surface area associated with the alternating circumferential section.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

Any and all patents, patent applications and printed publications referred to above are incorporated by reference herein.

What is claimed is:

1. A vascular prosthesis comprising:
    a generally tubular body defining an axis, the body placeable in contracted and expanded states and having an axial length and a circumferential dimension in the expanded state; and
    the body comprising:
        a series of circumferential elements including first, second, third and fourth circumferential elements, each circumferential element having first and second ends, the first and second ends being circumferentially spaced apart, each of circumferential element having a circumferentially-extending first length between the first and second ends;
        first and second connectors joining alternating ends of adjacent circumferential elements so that first connectors join the first ends of the first and second circumferential elements and the first ends of the third and fourth circumferential elements, and said second connector joins the second ends of the second and third circumferential elements, thereby creating a generally serpentine pattern of the circumferential elements and connectors;
        the first and second connectors having circumferentially-extending first and second connector lengths;
        the first length of the circumferential element plus the first and second connector lengths joined thereto equaling a total circumferential length; and
        each connector length being between 2.5% and 25% of the total circumferential length, whereby axial flexibility is provided for the body without sacrificing deployment dynamics;
        the second and third circumferential elements and the first connectors at the first ends of the second and third circumferential elements separated by a stress relief slot, each stress relief slot having a circumferentially-extending relief slot length of more than 50% and less than 95% of the total circumferential length; and
        the stress relief slots having narrow width portions over a majority of the relief slot lengths, the narrow width portions having constant-width lateral dimensions of no greater than about 3 mm.

2. The vascular prosthesis of claim 1, wherein the prosthesis comprises a shape memory material.

3. The vascular prosthesis of claim 1, wherein at least one of the circumferential elements and the connectors are essentially rectangular.

4. The vascular prosthesis of claim 1, wherein the circumferential elements and the connectors are essentially rectangular.

5. The vascular prosthesis of claim 1, in which the narrow width portion has a lateral dimension of less than 1 mm.

6. The vascular prosthesis of claim 1, in which the narrow width portion has a lateral dimension of less than 0.5 mm.

7. The vascular prosthesis of claim 1, in which the narrow width portions extend over essentially the entire relief slot lengths.

8. The vascular prosthesis of claim 1, wherein the first lengths are equal lengths.

9. The vascular prosthesis of claim 1, wherein the connector lengths are equal lengths.

10. The vascular prosthesis of claim 1, wherein the connectors are essentially triangular.

11. The vascular prosthesis of claim 1, wherein the connector at one end of the circumferential element overlaps with the connector at the other end of the circumferential element at a treatment vessel diameter.

12. The vascular prosthesis of claim 1, wherein the connector at one end of the circumferential element creates a gap with the connector at the other end of the circumferential element of less than 0.120" at a treatment vessel diameter.

13. The vascular prosthesis of claim 1, wherein the length of the circumferential element is essentially equal to its width.

14. The vascular prosthesis of claim 1, wherein the length of the circumferential element is more than two times greater than its width.

15. The vascular prosthesis of claim 1, wherein the circumferential elements include circumferentially extending slots with lengths more than 50% and less than 95% of the total circumferential length.

16. The vascular prosthesis of claim 1, wherein the widths of the circumferential elements vary along the longitudinal axis.

17. The vascular prosthesis of claim 1, wherein the total circumferential length varies along the longitudinal axis.

18. The vascular prosthesis of claim 1, wherein the total circumferential length decreases along the longitudinal axis.

19. The vascular prosthesis of claim 1, wherein the heights of circumferential elements vary along the longitudinal axis.

20. The vascular prosthesis of claim 1, wherein a series of circumferential elements transition to two independent series of circumferential elements to support a bifurcation.

21. The vascular prosthesis of claim 1, wherein:
    at least a plurality of said connectors have higher surface area over at least a portion of the connector compared to the circumferential elements, whereby strength and radiopacity at the connectors is enhanced.

22. The vascular prosthesis of claim 1, wherein the relief slot length is greater than ⅔ of the total circumferential length.

23. The vascular prosthesis of claim 1, wherein the stress relief slot has essentially mirrored sides over the majority of its length.

24. The vascular prosthesis of claim 1, wherein the narrow width portions of the stress relief slots have straight sides.

25. The vascular prosthesis of claim 1, wherein the stress relief slots have curved closed ends to limit stress concentration.

26. The vascular prosthesis of claim 25, wherein the body in the region surrounding the curved closed ends of the stress relief slots have higher surface areas than the average surface area for the rest of the body.

27. The vascular prosthesis of claim 25, wherein the curved closed ends of the stress relief slots are substantially free of holes for at least 0.25 mm.

28. The vascular prosthesis of claim 1, wherein the body in the region adjacent to the narrow width portion is substantially free of holes for at least 0.25 mm.

29. The vascular prosthesis of claim 1, wherein the stress relief slots have varying lengths.

30. A vascular prosthesis comprising:
    a generally tubular body defining an axis, the body placeable in contracted and expanded states and having an axial length and a circumferential dimension in the expanded state; and
    the body comprising:

a series of circumferential elements including first, second, third and fourth circumferential elements, each circumferential element having first and second ends, the first and second ends being circumferentially spaced apart, each of circumferential element having a circumferentially-extending first length between the first and second ends;

first and second connectors joining alternating ends of adjacent circumferential elements so that first connectors join the first ends of the first and second circumferential elements and the first ends of the third and fourth circumferential elements, and said second connector joins the second ends of the second and third circumferential elements, thereby creating a generally serpentine pattern of the circumferential elements and connectors;

the circumferential elements and the connectors being essentially rectangular;

the lengths of the circumferential elements being more than two times greater than their widths;

the first and second connectors having circumferentially-extending first and second connector lengths;

the first length of the circumferential element plus the first and second connector lengths joined thereto equaling a total circumferential length; and each connector length being between 2.5% and 25% of the total circumferential length, whereby axial flexibility is provided for the body without sacrificing deployment dynamics;

the second and third circumferential elements and the first connectors at the first ends of the second and third circumferential elements separated by a stress relief slot, each stress relief slot having a circumferentially-extending relief slot length of more than 50% and less than 95% of the total circumferential length;

the stress relief slots having curved closed ends to limit stress concentration; and the stress relief slots having narrow width portions over essentially the entire relief slot lengths, the narrow width portions having constant-width lateral dimensions of no greater than about 3 mm.

31. The vascular prosthesis of claim 30, wherein the total circumferential length decreases along the longitudinal axis.

* * * * *